United States Patent
Guimaraes

(10) Patent No.: US 9,192,746 B2
(45) Date of Patent: Nov. 24, 2015

(54) REPERFUSION CATHETER SYSTEM

(75) Inventor: Marcelo Silveira Guimaraes, Mount Pleasant, SC (US)

(73) Assignee: COOK MEDICAL TECHNOLOGIES LLC, Bloomington, IN (US)

( * ) Notice: Subject to any disclaimer, the term of this patent is extended or adjusted under 35 U.S.C. 154(b) by 237 days.

(21) Appl. No.: 12/858,156

(22) Filed: Aug. 17, 2010

(65) Prior Publication Data
US 2011/0301571 A1    Dec. 8, 2011

Related U.S. Application Data

(60) Provisional application No. 61/352,224, filed on Jun. 7, 2010.

(51) Int. Cl.
*A61M 25/10*    (2013.01)
*A61M 25/06*    (2006.01)

(52) U.S. Cl.
CPC ........... *A61M 25/10* (2013.01); *A61M 25/0662* (2013.01); *A61M 2025/0681* (2013.01)

(58) Field of Classification Search
CPC ............... A61M 2210/125; A61M 2025/1052; A61M 1/369; A61M 1/3653; A61M 2202/047; A61M 25/10; A61M 2025/1095; A61M 2025/1097; A61M 1/3621; A61M 1/3655; A61M 2025/0034; A61B 17/12136; A61B 2017/00243
USPC ................................................ 604/6.16, 509
See application file for complete search history.

(56) References Cited

U.S. PATENT DOCUMENTS 3,593,713 A    7/1971  Bogoff
4,763,648 A  *  8/1988  Wyatt ............................ 600/486

(Continued)

FOREIGN PATENT DOCUMENTS

CN    1298287 A    6/2001
CN    2576179 Y   10/2003

(Continued)

OTHER PUBLICATIONS

International Search Report based on corresponding PCT application No. PCT/US2011/039413 dated Nov. 14, 2011 (3 pgs).

(Continued)

*Primary Examiner* — Bhisma Mehta
*Assistant Examiner* — Bradley Osinski
(74) *Attorney, Agent, or Firm* — Brinks Gilson & Lione

(57) ABSTRACT

A reperfusion catheter system with an introducer sheath having an inner wall defining a longitudinal opening extending from a proximal portion to a distal end. A balloon catheter has an outer wall and has a longitudinal opening extending from a proximal portion to a distal end. The balloon catheter is disposed through the opening in the introducer sheath, and the balloon catheter has an inflatable balloon at the distal end. A conduit has a first end disposed in fluid communication with the area inside the introducer sheath between the inner wall of the introducer sheath and the outer wall of the balloon catheter. The conduit also has a second end disposed in fluid communication with the inside of the balloon catheter. The invention provides for the establishment of artificial antegrade blood flow in the lumen of a target vessel through a path between the outer wall of the balloon catheter and the inner wall of the introducer sheath, through the conduit, through the opening in the balloon catheter, and exiting through the distal end of the balloon catheter. When the occlusion balloon is inflated, there is no back flow in the target vessel and, as the artificial antegrade flow takes place, there is full control of the target vessel blood flow and as a result a significant increase in the safety of the embolization procedures.

17 Claims, 2 Drawing Sheets

(56) References Cited

U.S. PATENT DOCUMENTS

| | | | |
|---|---|---|---|
| 4,771,777 A | 9/1988 | Horzewski et al. | |
| 5,021,045 A | 6/1991 | Buckberg et al. | |
| 5,106,363 A | 4/1992 | Nobuyoshi | |
| 5,137,513 A | 8/1992 | McKinnis et al. | |
| 5,211,631 A | 5/1993 | Sheaff | |
| 5,403,274 A | 4/1995 | Cannon | |
| 5,421,825 A | 6/1995 | Farcot | |
| 5,597,377 A | 1/1997 | Aldea | |
| 5,637,086 A | 6/1997 | Ferguson et al. | |
| 5,702,361 A * | 12/1997 | Evans et al. | 604/508 |
| 5,891,154 A | 4/1999 | Loeffler | |
| 6,017,977 A | 1/2000 | Evans et al. | |
| 6,083,215 A | 7/2000 | Milavetz | |
| 6,129,700 A | 10/2000 | Fitz | |
| 6,190,357 B1 | 2/2001 | Ferrari et al. | |
| 6,330,884 B1 | 12/2001 | Kim | |
| 6,436,071 B1 | 8/2002 | Schwartz | |
| 6,461,327 B1 | 10/2002 | Addis et al. | |
| 6,622,367 B1 | 9/2003 | Bolduc et al. | |
| 7,789,846 B2 | 9/2010 | Solar et al. | |
| 7,867,246 B2 | 1/2011 | Kim | |
| 8,968,378 B2 | 3/2015 | Ginsburg et al. | |
| 2003/0040762 A1 | 2/2003 | Dorros et al. | |
| 2005/0004503 A1* | 1/2005 | Samson et al. | 604/6.14 |
| 2005/0131453 A1 | 6/2005 | Parodi | |
| 2005/0228402 A1 | 10/2005 | Hofmann | |
| 2006/0167398 A1* | 7/2006 | Solar et al. | 604/6.13 |
| 2006/0167399 A1* | 7/2006 | Solar et al. | 604/6.13 |
| 2006/0270966 A1* | 11/2006 | Bolling et al. | 604/9 |
| 2009/0054918 A1* | 2/2009 | Henson | 606/159 |

FOREIGN PATENT DOCUMENTS

| | | | |
|---|---|---|---|
| CN | 101631584 A | 1/2010 | |
| JP | 63238877 A2 | 10/1988 | |
| JP | 1170473 A | 7/1989 | |
| JP | 2102670 A2 | 4/1990 | |
| JP | 3190332 A | 8/1991 | |
| JP | 2000506514 A | 5/2000 | |
| JP | 2002523138 A | 7/2002 | |
| JP | 2005500138 A | 1/2005 | |
| JP | 2008528129 A | 7/2008 | |
| WO | 9220398 A1 | 11/1992 | |
| WO | 01/13983 A2 | 3/2001 | |
| WO | 03018085 A2 | 3/2003 | |
| WO | 2006081288 A2 | 8/2006 | |

OTHER PUBLICATIONS

International Preliminary Report on Patentability and Written Opinion from corresponding PCT application No. PCT/US2011/039413 dated Dec. 20, 2012 (8 pgs).

European Patent Office, Supplementary Partial European Search Report, Mailed on Mar. 21, 2014, 5 pages.

Japanese Patent Office, English Translation of Office Action dated Nov. 25, 2013, for Japanese Patent Application No. 2013-514292, 5 pages.

Japanese Patent Office, English Translation of Office Action dated Apr. 1, 2014, for Japanese Patent Application No. 2013-514292, 6 pages.

Noboru Ogata, Katsumi, Goto, Current and Future Perspective of Interventional Neuroradiology, Newmed, M-E Promote Association Co., Ltd., Teizo Imamoto, vol. 19, No. 10, 1992. (no English language translation available).

Kouji Takahashi, Makoto Furuse, Tamio Aburano, Refresher Course, Diagnosis of Pulmonary Arteriovenous Fistula and IVR, Diagnostic Imaging, Chihiro Mizutani, Shujunsha, vol. 19, No. 10, 1999. (no English language translation available).

* cited by examiner

REPERFUSION CATHETER SYSTEM

CROSS-REFERENCE TO RELATED APPLICATION

The present application claims priority benefit of U.S. Provisional Patent Application No. 61/352,224 filed Jun. 7, 2010, which is entitled "Reperfusion Catheter System" and is incorporated herein by reference.

FIELD OF THE INVENTION

The present invention relates generally to medical devices and specifically to a catheter system for all types of embolization procedures including, but not limited to, chemo-embolization, radio-embolization, embolization of high flow blood vessels, situations where there is a high risk of non-target embolization, apparently safe situations in which a non-target embolization might lead to severe complications, and interventional oncology procedures where microparticles (type of embolic agent) with chemotherapy or with radiation are injected into tumor vessels.

BACKGROUND OF THE INVENTION

In the case of standard catheter embolization procedures, there is a possibility of having backflow causing non-target embolization. This backflow may be caused by inadequate techniques employed by the person performing the treatment. Also, where pressure builds up distally such as with embolization procedures with microparticles and liquid embolic agents (glue/Onyx [Ev3]) backflow may result. This backflow may also result in non-target embolization. In order to prevent backflow, an occlusion balloon catheter may be used in the target vessel. However, inflation of the balloon stops the blood flow to the organs and or tissues of the target vessel which introduces additional risks.

Accordingly, there is a need for a catheter system that allows full control of the target vessel antegrade flow (either decreasing the antegrade flow or stopping it completely when needed) to aid in deploying embolic agents and to provide perfusion to a vessel occluded by a balloon.

SUMMARY OF THE INVENTION

The present invention solves the above-described need by providing artificial antegrade flow in the target vessel. The flow provides perfusion to the tissue and organs and is used to aid the embolic agent in reaching the target area. The invention simultaneously combines no back flow when the balloon is insufflated, full embolization control, and enhanced safety. Once the artificial antegrade blood vessel flow is established, a micro catheter may be introduced through the occlusion balloon catheter, in a coaxial manner, up to the target blood vessel and embolization using standard techniques may be performed.

The present invention includes a reperfusion catheter system with an introducer sheath having a longitudinal opening extending from a proximal portion to a distal end. A balloon catheter, which has a longitudinal opening extending from a proximal portion to a distal end, is disposed through the opening in the introducer sheath. The balloon catheter has an inflatable balloon at the distal end. A conduit has a first end disposed in fluid communication with the area inside the introducer sheath between an inner wall of the introducer sheath and an outer wall of the balloon catheter. The conduit also has a second end disposed in fluid communication with the inside of the balloon catheter. The invention provides for the establishment of artificial antegrade blood flow in a lumen of a target vessel through a path between the outer wall of the balloon catheter and the inner wall of the introducer sheath, through the conduit, through the opening in the balloon catheter, and exiting through the distal end of the balloon catheter.

BRIEF DESCRIPTION OF THE DRAWINGS

The invention is illustrated in the drawings in which like reference characters designate the same or similar parts throughout the figures of which.

DETAILED DESCRIPTION OF THE INVENTION

Figure 1:
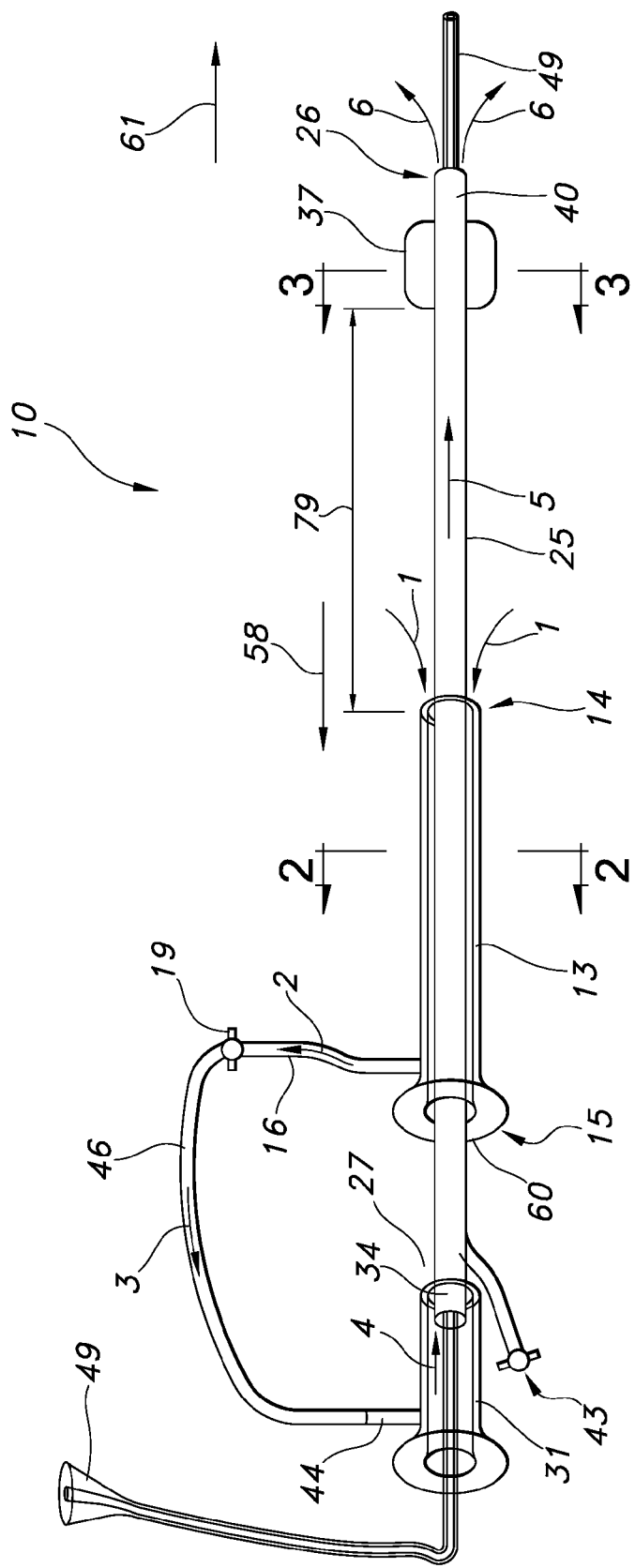
FIG. 1 is a side schematic view of the system of the present invention.
Figure 2:
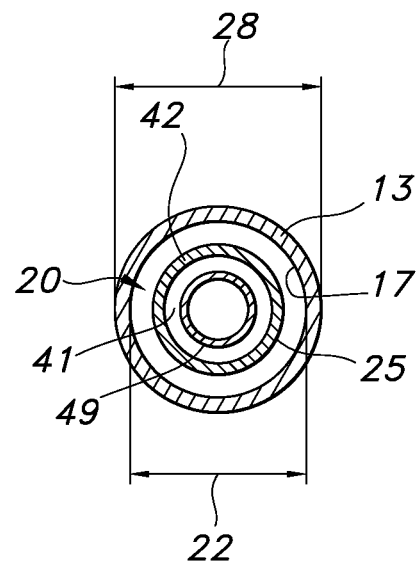
FIG. 2 is a cross-sectional view taken along lines 2-2 of FIG. 1.

Referring to the figures and initially to FIG. 1, the reperfusion catheter system 10 includes an introducer sheath 13 having an inner wall 17 (FIG. 2) defining a longitudinal opening 20 (FIG. 2). The introducer sheath 13 has a distal end 14 and a proximal portion 15. A lateral check flow 16 including a stopcock 19 is positioned in the proximal portion 15. The longitudinal opening 20 extends from the proximal portion 15 to the distal end 14. The lateral check flow 16 is a side port that may be integrally formed with or attached to the introducer sheath 13. The introducer sheath 13 may be shorter in length than a typical introducer sheath in order to maximize the artificial antegrade blood flow as described in greater detail hereinafter.

Figure 3:
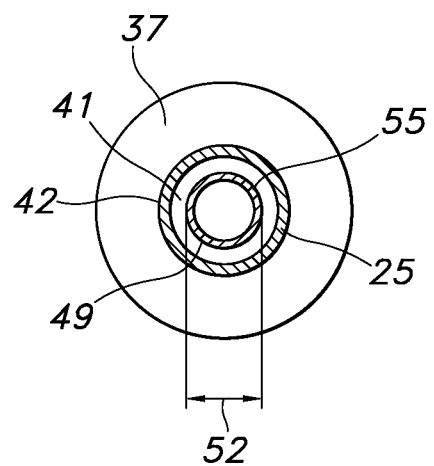
FIG. 3 is a cross-sectional view taken along lines 3-3 of FIG. 1.

The introducer sheath 13 has the largest inner diameter 22 (FIG. 2) possible in order to allow antegrade blood flow around an occlusion balloon catheter 25 that is inserted through the opening 20 in the introducer sheath 13. The outer diameter 28 of the introducer sheath 13 is as small as possible in order to have a low profile and to minimize puncture site complications. The flexible occlusion balloon catheter 25 has a distal end 26 and a proximal portion 27. A detachable valve system 31 (for example, a Touhy-Borst adapter) attaches at a hub 34 in the proximal portion 27 of the balloon catheter 25 and has a compliant balloon 37 at a tip 40 on the distal end 26. The balloon catheter 25 has a longitudinal opening 41 (FIG. 3) and an outer wall 42 (FIG. 2). The balloon 37 can be inflated through a side port 43. The side port 43 intersects with the balloon catheter 25 at the proximal portion 27. The valve system 31 has a side port 44. A connecting tube 46 extends between the side port 44 on the valve system 31 and the lateral check flow 16 of the introducer sheath 13. This connection allows the blood to flow from the introducer sheath 13 (which, for example, may be located in the lumen of the femoral artery) through the connecting tube 46 into the balloon catheter 25 and exiting through the tip 40 of the occlusion balloon catheter 25 at the target vessel location.

A micro catheter 49 may be inserted through the opening 41 in the occlusion balloon catheter 25 to allow embolization with microparticles, micro coils or liquid embolic agents (glue or Onyx [Ev3]). The outer diameter 52 (FIG. 3) of the micro catheter 49 is preferably minimized. Also, the outer wall 55 (FIG. 3) of the micro catheter 49 is preferably made as thin as possible as long as there is no compromise in push ability and the ability to deliver embolic agents. Alternatively, embolic agents can be delivered through the occlusion balloon catheter 25 such as the existing Amplatzer Vascular Plug (AGA) or 0.035" coils as will be evident to those of ordinary skill in the art based on this disclosure. The catheter system 10 of the present invention is preferably comprised of polymers that provide the specific features of diameter compatibility, flexibility, torque-ability, and optimized blood flow.

In operation the system is used as follows. Once vascular access has been obtained (either arterial/venous), the introducer sheath 13 is introduced to secure the access. In the blood vessel lumen where the introducer sheath 13 is introduced (e.g. the femoral artery), the normal blood flow is in the direction of arrow 58. Using standard catherization techniques as will be known to those of ordinary skill in the art based on this disclosure, the occlusion balloon catheter 25 is advanced selectively up to the target vessel. At the target vessel lumen, the normal blood flow is in the direction of arrow 61. The distance between the position where vascular access is obtained (e.g., the femoral artery) and the target vessel varies depending on the location of the target vessel. Accordingly, the length 79 of the balloon catheter 25 between the distal end 14 of the introducer sheath 13 and the balloon 37 will vary depending on how far the balloon catheter 25 is extended into the vasculature as will be evident to those of ordinary skill in the art based on this disclosure. Once the balloon catheter 25 is deployed to the target vessel, the lateral check flow 16 of the introducer sheath 13 may be connected into the valve system 31 (for example, a Tuohy-Borst adaptor) by means of the connecting tube 46. An adapter such as, for example, a Luer-lock attaches the valve system 31 to the hub 34 of the occlusion balloon catheter 25. At this point, the occlusion balloon catheter 25 (it has a compliant balloon 37 in the tip 40) is insufflated to stop the blood flow in the target vessel. The introducer sheath lateral check flow 16 is open and the valve system 31 will allow blood coming from the common femoral artery to flow through the reperfusion catheter system 10 into the target vessel.

The above-identified technique provides an artificial/diverted antegrade flow towards the target vessel that is important to aid the embolic agent in reaching the target area distally, such as for treating a tumor microvasculature. Without having back blood flow in the target vessel when the balloon 37 of the occlusion balloon catheter 25 is insufflated, there is a remarkable enhancement in procedure safety (antegrade flow, no back flow).

The flow path for the blood is indicated by arrows numbered 1-6 in FIG. 1. As indicated by arrow 1, the blood flows into the lumen of the introducer sheath 13 and flows between the outer wall 42 of the balloon catheter 25 and the inner wall 17 of the introducer sheath 13. From the inside of the introducer sheath 13, the blood flows into the lateral check flow 16 to the stopcock 19 as indicated by arrows 2. The blood cannot flow through the introducer sheath 13 past the lateral check flow 16 because the proximal end 60 is sealed as will be evident to those of ordinary skill in the art based on this disclosure. As indicated by arrows 3, after the blood exits the lateral check flow 16 it passes through the connecting tube 46 to the valve assembly 31. The blood passes through the valve assembly 31 into the balloon catheter 25 as indicated by arrows 4. The blood then travels through the balloon catheter 25 as indicated by arrows 5 and exits at the tip 40 of the balloon catheter 25 as indicated by arrows 6.

Once the artificial antegrade blood vessel flow is established, a micro catheter 49 may be introduced through the occlusion balloon catheter 25 in a coaxial manner up to the target blood vessel and embolization using standard techniques can be performed. In a high flow blood vessel, the balloon insufflation permits flow control. As there is no retrograde or backflow there is full control to avoid non-target embolization that may potentially happen at any time during the current embolization techniques using the existing devices available in the market. The balloon 37 may be deflated at any time if needed, and the inherent/native antegrade blood vessel flow can be reestablished immediately.

While the invention has been described in connection with certain embodiments, it is not intended to limit the scope of the invention to the particular forms set forth, but, on the contrary, it is intended to cover such alternatives, modifications, and equivalents as may be included within the spirit and scope of the invention as defined by the appended claims.

What is claimed is:

1. A reperfusion catheter system, comprising:
    an introducer sheath having an inner wall defining a longitudinal opening extending from a proximal portion to a distal end;
    a balloon catheter having an outer wall and having a longitudinal opening extending from a proximal end to a distal end, the balloon catheter disposed through the opening in the introducer sheath, the balloon catheter having an inflatable balloon at the distal end, the balloon catheter configured to allow a catheter to be inserted through the entire opening of the balloon catheter from the proximal end of the balloon catheter to the distal end of the balloon catheter;
    a conduit having a first end disposed in fluid communication with the inside of the introducer sheath and having a second end disposed in fluid communication with the inside of the balloon catheter;
    wherein antegrade blood flow is established in a lumen of a target vessel through a path between the inside of the introducer sheath, through the conduit, through the opening in the balloon catheter, and exiting through the distal end of the balloon catheter;
    wherein the conduit includes a lateral check flow member extending laterally from the introducer sheath, the check flow member having a stopcock at an end of the lateral check flow member opposite the introducer sheath, the conduit further including a single connecting tube having first and second ends and extending between the stopcock and a side port of a valve system, wherein the first end is attached to the stopcock and the second end is attached to the side port of the valve system, wherein the valve system attaches to the proximal end of the balloon catheter;
    wherein substantially all of the blood flowing through the conduit reaches the longitudinal opening of the balloon catheter and does not branch off into other branches of other conduits.

2. The reperfusion catheter system of claim 1, wherein the first end of the conduit is disposed in fluid communication with an area inside the introducer sheath between the inner wall of the introducer sheath and the outer wall of the balloon catheter.

3. The reperfusion catheter system of claim 1, further comprising a micro catheter disposed through the opening in the balloon catheter.

4. The reperfusion catheter system of claim 1, further comprising a side port integrally formed in the introducer sheath.

5. The reperfusion catheter system of claim 1, further comprising a tip at the distal end of the balloon catheter, the tip having a diameter smaller than the diameter of the balloon catheter.

6. The reperfusion catheter system of claim 1, further comprising an embolic agent carried by the balloon catheter.

7. The reperfusion catheter system of claim 6, wherein the embolic agent is a micro coil.

8. The reperfusion catheter system of claim 6, wherein the embolic agent is a micro particle.

9. The reperfusion catheter system of claim 6, wherein the embolic agent is a liquid.

10. The reperfusion catheter system of claim 6, wherein the embolic agent is an Amplatzer vascular plug.

11. The reperfusion catheter system of claim 1, wherein the valve system is a Tuohy-Borst adaptor.

12. A reperfusion catheter system, comprising:
an introducer sheath having an inner wall defining a longitudinal opening extending from a proximal portion to a distal end;
a balloon catheter having an outer wall and having a longitudinal opening extending from a proximal end to a distal end, the balloon catheter disposed through the opening in the introducer sheath, the balloon catheter having an inflatable balloon at the distal end;
a conduit having a first end disposed in fluid communication with the inside of the introducer sheath and having a second end disposed in fluid communication with the inside of the balloon catheter;
a micro catheter disposed through the entire opening of the balloon catheter and through the proximal end of the balloon catheter and out of the distal end of the balloon catheter;
wherein antegrade blood flow is established in a lumen of a target vessel through a path between the inside of the introducer sheath, through the conduit, through the opening in the balloon catheter, and exiting through the distal end of the balloon catheter;
wherein the conduit includes a lateral check flow member extending laterally from the introducer sheath, the check flow member having a stopcock at an end of the lateral check flow member opposite the introducer sheath, the conduit further including a single connecting tube having first and second ends and extending between the stopcock and a side port of a valve system, wherein the first end is attached to the stopcock and the second end is attached to the side port of the valve system, wherein the valve system attaches to the proximal end of the balloon catheter;
wherein substantially all of the blood flowing through the conduit reaches the longitudinal opening of the balloon catheter and does not branch off into other branches of other conduits.

13. The reperfusion catheter system of claim 12, wherein the first end of the conduit is disposed in fluid communication with an area inside the introducer sheath between the inner wall of the introducer sheath and the outer wall of the balloon catheter.

14. The reperfusion catheter system of claim 12, further comprising a side port integrally formed in the introducer sheath and the lateral check flow member extends from the side port.

15. The reperfusion catheter system of claim 12, further comprising a tip at the distal end of the balloon catheter, the tip having a diameter smaller than the diameter of the balloon catheter.

16. The reperfusion catheter system of claim 12, further comprising an embolic agent carried by the micro catheter.

17. A reperfusion catheter system, comprising:
an introducer sheath having an inner wall defining a longitudinal opening extending from a proximal portion to a distal end;
a balloon catheter having an outer wall and having a longitudinal opening extending from a proximal end to a distal end, the balloon catheter disposed through the opening in the introducer sheath, the balloon catheter having an inflatable balloon at the distal end, the balloon catheter configured to allow an embolic agent to be inserted through the entire opening of the balloon catheter from the proximal end of the balloon catheter and to be delivered through the distal end of the balloon catheter;
a conduit having a first end disposed in fluid communication with the inside of the introducer sheath and having a second end disposed in fluid communication with the inside of the balloon catheter;
wherein antegrade blood flow is established in a lumen of a target vessel through a path between the inside of the introducer sheath, through the conduit, through the opening in the balloon catheter, and exiting through the distal end of the balloon catheter;
wherein the conduit includes a lateral check flow member extending laterally from the introducer sheath, the check flow member having a stopcock at an end of the lateral check flow member opposite the introducer sheath, the conduit further including a single connecting tube having first and second ends and extending between the stopcock and a side port of a valve system, wherein the first end is attached to the stopcock and the second end is attached to the side port of the valve system, wherein the valve system attaches to the proximal end of the balloon catheter;
wherein substantially all of the blood flowing through the conduit reaches the longitudinal opening of the balloon catheter and does not branch off into other branches of other conduits.

\* \* \* \* \*